United States Patent [19]
Fukuda

[11] Patent Number: 5,808,312
[45] Date of Patent: Sep. 15, 1998

[54] SYSTEM AND PROCESS FOR INSPECTING AND REPAIRING AN ORIGINAL

[75] Inventor: Yasuaki Fukuda, Utsunomiya, Japan

[73] Assignee: Canon Kabushiki Kaisha, Tokyo, Japan

[21] Appl. No.: 677,526

[22] Filed: Jul. 10, 1996

[30] Foreign Application Priority Data

Jul. 14, 1995 [JP] Japan .................................. 7-178691
Jun. 14, 1996 [JP] Japan .................................. 8-154074

[51] Int. Cl.⁶ .................................................. G21K 7/00
[52] U.S. Cl. ........................................ 250/492.2; 378/43
[58] Field of Search ........................... 250/492.2; 378/43

[56] References Cited

U.S. PATENT DOCUMENTS

| | | | |
|---|---|---|---|
| 4,548,883 | 10/1985 | Wagner | 250/492.2 |
| 5,123,036 | 6/1992 | Uno et al. | 378/34 |
| 5,177,774 | 1/1993 | Suckewer et al. | 378/43 |

*Primary Examiner*—Jack I. Berman
*Attorney, Agent, or Firm*—Fitzpatrick, Cella, Harper & Scinto

[57] ABSTRACT

An original inspecting and repairing system includes an inspecting device having at least one of a vacuum ultraviolet ray microscope and an X-ray microscope, for inspecting an original, and a processing device for processing the original on the basis of the inspection. This practically enables inspection and repair of any fault of a reflection type original.

23 Claims, 2 Drawing Sheets

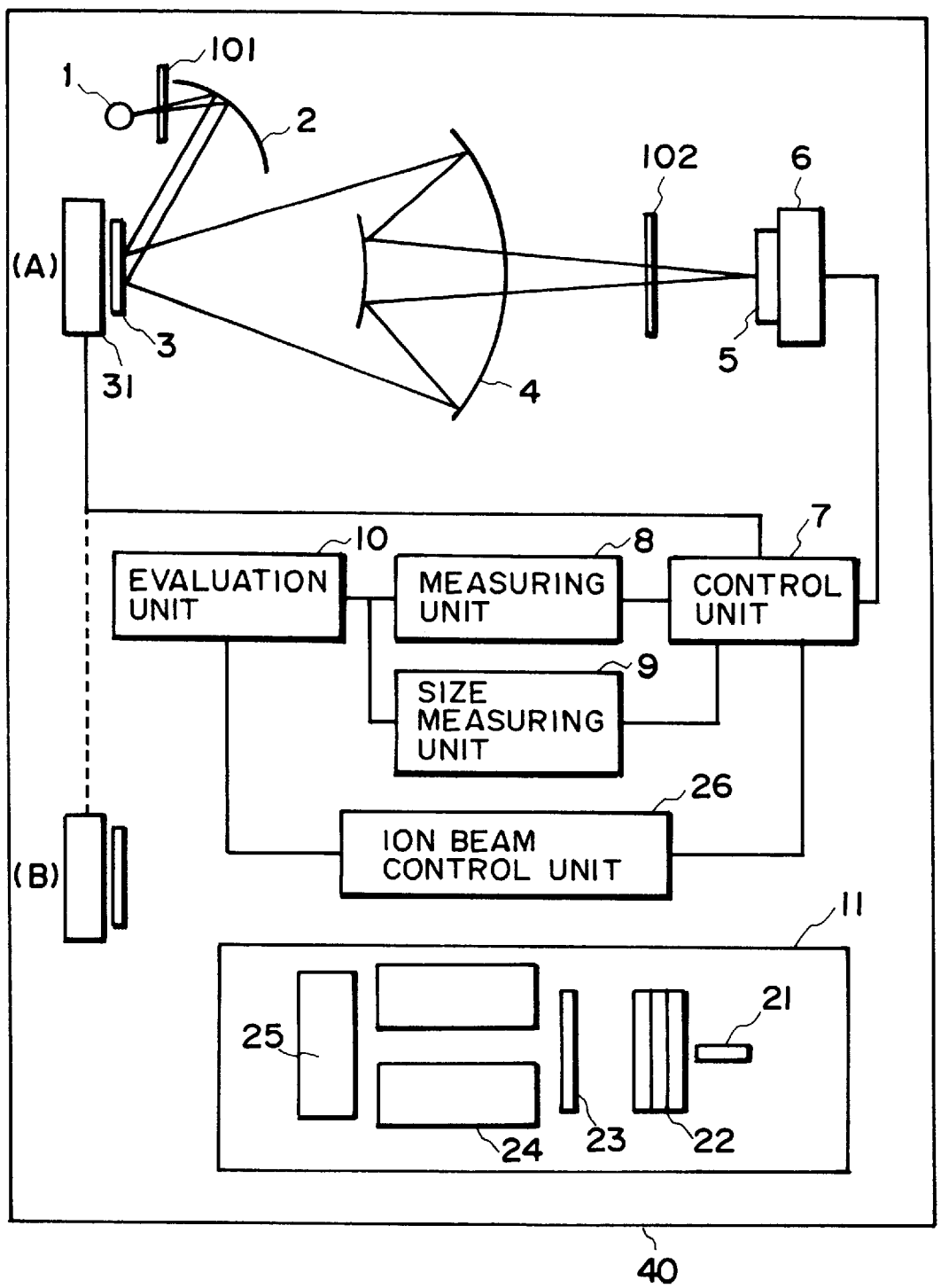
F I G. 1

SYSTEM AND PROCESS FOR INSPECTING AND REPAIRING AN ORIGINAL

FIELD OF THE INVENTION AND RELATED ART

This invention relates to a system and a process for inspecting and repairing an original, such as a mask or reticle to be used in lithographic transfer of a pattern with radiation, such as ultraviolet rays or X-rays.

Lithographic process is dominantly used in the manufacture of microdevices, such as semiconductor devices as a process for forming a fine pattern, and it uses an original, such as a mask or reticle. The originals used in this process are classified into two types, i.e., the transmission type and the reflection type.

Transmission type originals are produced by forming a pattern, such as a circuit pattern to be transferred, of metal thin film, for example, upon the surface of a transmissive substrate material, such as silica, for example. This thin film serves as a light blocking material used for the exposure process.

Generally, the transmissivity of this light blocking material to exposure light can be made small on the order of about $1/1000$. Thus, it is possible to make an evaluation of a mask by evaluating the shape of the pattern. Namely, even for a fine pattern, evaluation of an original with required precision can be performed by using a high-magnification and high-precision measuring system, such as an electron microscope, for example. Based on this principle, optical reticle evaluation apparatuses or electron beam mask inspecting systems have been practically used.

As regards reflection type originals, on the other hand, there is a possibility that the reflectivity distribution of a multilayered film reflection mirror, which is the substrate of the original, involves non-uniformness due to the fault of the multilayered film. Additionally, as regards the pattern formed on the original, the reflectivity characteristic and geometrical shape thereof do not necessarily correspond to each other. For these reasons, sufficient evaluation is difficult to achieve through a conventional pattern inspection processes wherein evaluation is done only with respect to the shape as detected by visible light or a low contrast of a secondary electron beam.

What is to be done in the inspection of a reflection type original is to check (i) that the reflectivity of the substrate is uniform over the whole surface; (ii) that the shape of a circuit pattern to be transferred or of a portion other than the pattern corresponds to the shape as designed; and (iii) that the reflectivity at the pattern or at a portion other than the pattern satisfies a predetermined specification. In conventional fault repairing processes for reflection type originals, an original is practically used in a lithographic process and the shape of a resultant resist image is measured and evaluated. Based on the measurement and evaluation, any fault is discriminated and, then, it is repaired. This requires complicated operations.

SUMMARY OF THE INVENTION

It is accordingly an object of the present invention to provide a system and/or a process which practically enables inspection and repair of a reflection type original.

It is another object of the present invention to provide a device manufacturing method which uses an original inspecting and repairing process such as described above.

In accordance with an aspect of the present invention, there is provided an original inspecting and repairing system, comprising: inspecting means having at least one of a vacuum ultraviolet ray microscope and an X-ray microscope, for inspecting an original; and processing means for processing the original on the basis of the inspection.

In accordance with another aspect of the present invention, there is provided an original inspecting method, comprising the steps of: providing one of a vacuum ultraviolet ray microscope and an X-ray microscope; and inspecting a reflection type original by using the microscope.

The inspection may be made to inspect any fault of the reflection type original.

The inspection may be made to inspect any fault of a multilayered reflection film of the reflection type original.

The method may further comprise repairing the original on the basis of said inspection.

In accordance with a further aspect of the present invention, there is provided an original having been inspected and repaired by an original inspecting method as recited above.

In accordance with a further aspect of the present invention, there is provided a device manufacturing method for manufacturing devices by using an original inspected and repaired by an original inspecting method as recited above.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is a schematic and diagrammatic view of an original inspecting and repairing system according to an embodiment of the present invention.

DESCRIPTION OF THE PREFERRED EMBODIMENTS

Figure 2:
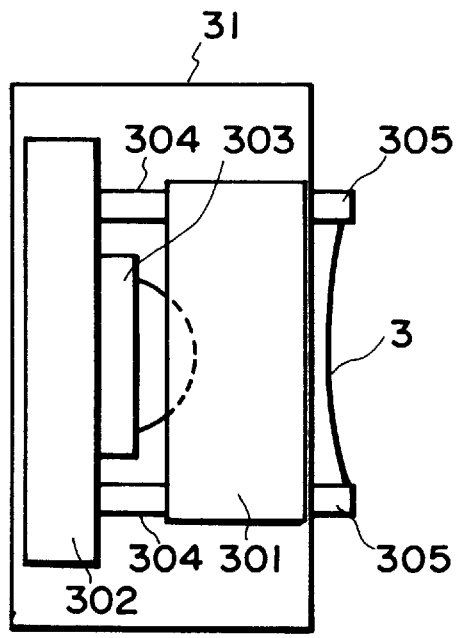
FIG. 2 is a schematic view of a tilt mechanism mounted on a stage.

Vacuum ultraviolet ray or soft X-ray technology has recently advanced and microscopes using such spectral region are being developed. Theses microscopes are intended to be used for plasma diagnosis or biological cell observation, and, in such microscopes, for observation, an enlarged image is formed on a photographic film or an imaging plate, for example.

Briefly, the present invention uses such a principle. In the present invention, a radiation beam from a light source such as ultraviolet rays or soft X-rays may be projected on a reflection type original, and a reflection beam from the original may be imaged on a detector. On the basis of a calibrated magnification, the size of the image may be measured precisely and, from the measured size and from a reflection light intensity signal, the shape and reflectivity of the pattern may be measured. Then, the shape may be compared with design data of the original, and any fault there may be identified. If the reflectivity of the pattern is less than a predetermined amount, the pattern may be discriminated as being at fault and a stage, holding the original, may be moved to a micro-processing system in which the fault of the pattern may be repaired by using photons or charged particles (electrons or ions).

The fault of the pattern of the original may then be repaired. Pattern fault may comprise one of a solid fault, wherein a non-reflective material is deposited at an unwanted position, and a blank fault, wherein a necessary non-reflective material is void. In either case, such a fault may be discriminated on the basis of the result of inspection by a juxtaposed original inspecting system. As regard the former fault, an energy beam being narrowed to a small diameter may be projected from the outside to the fault, to cause evaporation thereof to remove it. As regards the latter fault, a non-reflective material may be deposited into a film to provide a required shape, by which the pattern is repaired.

In these processes, the stage may be moved from the inspecting position to the repairing position without unloading the original from the stage, such that the inspection and repair may be performed successively. This may be effective to perform repair of an original without being affected by distortion or positional deviation due to re-setting of the original.

A fault of a reflection type original may reside not only in the pattern portion as described above but also in a multi-layered reflection film itself (the base of reflection type original). For example, a fault may frequently be observed in a multilayered film which fault may be attributable to a particle remaining on the substrate after cleaning, or to a strain created by evaporation of a water drop. Such fault may cause a variation in the reflectivity of the reflection mirror and, as a result of it, there may occur non-uniformness in the reflection intensity of the original. While such a fault may desirably be removed completely prior to the formation of the multilayered film, practically it is difficult to accomplish. Thus, the inspection and repair may desirably be performed not only to a pattern portion but also to a multilayered film reflection mirror portion which is the base of the reflection type original.

Preferred embodiments of the present invention will be described below.

FIG. 1 illustrates a specific structure of an embodiment of the present invention. Denoted in FIG. 1 at 1 is a light source which produces light of the same or similar wavelength as that used for the exposure process. Denoted at 2 is an illumination optical system for enlarging or reducing the light from the light source 1 and projecting the same to the surface of an original 2 to be inspected. Denoted at 101 is a filter for restricting the spectrum of illumination light, and it also has a function of a stop member for adjusting the light quantity and an illumination region to be defined. Denoted at 31 is a stage for holding the original 2 and for moving the same in vertical and horizontal directions. Denoted at 4 is a microscope optical system for imaging reflection light upon a detector. Denoted at 5 is a detector for detecting the reflection light, and denoted at 102 is a shutter which serves as a light blocking plate for blocking the light directed toward the detector, and which also serves as a restricting member for restricting the irradiation time. Denoted at 6 is a movable stage on which the detector 5 is mounted. Denoted at 7 is a control unit for controlling the measuring system as a whole during the sequential measurement operations and for storing and memorizing data of signals detected in the measurement. Denoted at 8 is a processing unit for processing the output of the detector into an image data, and denoted at 9 is a size measuring unit for measuring the size of a pattern on the basis of the image data. Denoted at 10 is an evaluation unit which has a function for comparing the measurement result with a design pattern shape and for producing a corresponding output as well as a function for discriminating goodness/badness on the basis of the comparison with the design data and with respect to predetermined discrimination reference data. These components provide an inspecting system.

On the other hand, denoted at 21 is an ion source, and denoted at 22 is a drawing electrode. Denoted at 23 is an acceleration electrode, and denoted at 24 is a deflection coil. Denoted at 25 is a convergent electron (ion) optical system, and denoted at 26 is an ion beam control unit. These components provide a micro-processing system 11.

Denoted at 40 is a vacuum chamber. In order to prevent attenuation of illumination light in the inspecting system and also to prevent impingement and scattering of ions flying in the micro-processing system with air, both the inspecting system and the micro-processing system are disposed in the same vacuum chamber 40. The stage 31 is adapted to be moved between a position A adjacent to the inspecting system and a position B adjacent to the micro-processing system, while holding thereon the original 3 to be inspected and repaired.

The structure and operation will be explained in greater detail.

The light source 1 produces light of the same or equivalent wavelength as the exposure wavelength practically used in an exposure apparatus for the manufacture of devices. It comprises a plasma X-ray source, for example, wherein a second harmonic of a YAG laser (wavelength 1.06 micron) is used as an excitation source and a target of tungsten is used. In place of this, an excimer laser, a free-electron laser, a synchrotron radiation producing device or an ArF excimer laser, for example, may be used, provided that it produces light in any of the regions from vacuum ultraviolet to soft X-ray. Beryllium (Be) filter 101 of a thickness 100 nm may be disposed in the light path to intercept light of longer wavelengths.

The illumination system 2 comprises a reflection optical system for illuminating the reflection type original 3, to be inspected, with uniform illuminance. It uses a multilayered film mirror (peak wavelength 13 nm) having a 4.5 layer pair of Si and Mo, to provide a Koehler illumination optical system. Particularly, because the laser light source has a small size light source, a fly's-eye mirror system, wherein a number of small multilayered film mirror are arrayed along a curved plane, may be used for uniformization of the illumination light. As regards a multilayered film for an optical element, a smaller number of layers may be selected so as not to excessively narrow the bandwidth of the reflection wavelength. The Koehler illumination may be replaced by critical illumination or coherent illumination, for example.

The original 3 is fixedly held by the stage 31, and a desired portion of the original 31 surface can be observed. The microscope optical system 4 comprises a Schwarzschild optical system having a magnification ×50. Like the illumination system, it uses a multilayered film mirror having a 4.5 layer pair. If the light source has a low luminance and the reflectivity should be made higher, the layer number may preferably be set to about 10.5–50.5.

The pattern of the reflection type original as illuminated by the illumination optical system is imaged in an enlarged scale on the detector 4, by the imaging optical system. The detector 5 comprises a two-dimensional image sensor of CCD, in this example. With this arrangement, the intensity of reflection light from the pattern of the reflection type original can be measured and, additionally, the size of the pattern can be measured. Thus, the data necessary for evaluation of the original is obtainable. The pattern of a reflection type original has a magnification which is inverse to the exposure reduction ratio. For an original to be used in 1:5 reduction system, the pattern size is five times, which in turn is magnified by ×50 by means of the microscope. Thus, a pattern of a magnified size 5×50=250 may be measured. As an example, for observation of an original with an actual circuit pattern of a pattern size 0.06 micron, it is observed on the microscope detector in a size 15 micron. This is sufficient to enable measurement of the reflectivity distribution on the CCD of the detector 5. The CCD of the detector 5 may be replaced by a photodiode, an image multiplier tube (image intensifier), or a micro-channel plate (MCP), for example. If an image multiplier tube is used, as an example, the overall magnification for inspection can be made larger (e.g., =1000), such that the reflectivity at respective points may be measured with higher precision and the measurement time may be reduced.

The distribution of reflection light intensity over the whole surface of the original is measured by scanningly moving, in the intensity measurement operation, the stage which holds the original and the stage which holds the detector simultaneously at a ratio corresponding to the imaging magnification ratio. The resultant data is analyzed into a distribution of reflection light quantity at respective points on the original, and those points having a predetermined reflectivity (e.g., 40%) or more are evaluated as effective pattern points, from which the pattern size is displayed. The distribution of the pattern is displayed in the form of numerical data or two-dimensional imagewise information. If necessary, the imagewise information may be outputted into a hard copy. On the other hand, the design data of the original pattern is inputted separately into the evaluation unit 10 in which it is compared with the pattern size, the pattern position or the pattern precision having been measured. The one as determined as satisfying the specification, on the basis of the comparison, is discriminated as being good.

The reflectivity is given in terms of a ratio between the incident light intensity and the reflected light intensity. If the incident light changes, the reflectivity also changes apparently. In consideration of this, a certain point on the original is selected as a measurement reference point. During the inspection process, the reflection light intensity at the measurement reference point is measured at a suitable frequency, to thereby detect any change in the incident light intensity, for reflectivity calibration.

Subsequent to the inspection of original described above, repair of pattern is performed.

The stage is moved from the position A adjacent to the inspecting system to the position B adjacent to the micro-processing system, without unloading the original from the stage. The measured data obtained at the inspecting system is directly transferred to the micro-processing system, and it is used as a mapping data which represents the fault to be repaired.

In the micro-processing system, a material such as a gallium, silicone or gold, for example, is ionized at the ion source 21 to emit ions. The ions are accelerated by the acceleration electrode 23 with an acceleration voltage 1–100 KV and, thereafter, they are deflected and converged by means of the deflection coil 24 and the optical system 25. A resultant convergent ion beam of 10–100 nm is used for repairing processing of a fault. While this embodiment uses a convergent ion beam, it may be replaced by an excimer laser (KrF or ArF) or an electron beam.

As for a solid fault, excessive non-reflective film material at such a solid fault is removed in accordance with the mapping data. The beam may have a radius 50 nm. The fault is scanned by the beam whereby it is removed. For every 10×10 micron region, the stage may be moved, and solid faults, if any, may be repaired successively.

As for blank faults (which may usually less than solid faults), on the other hand, a gas of organic gold compound may be blown to the substrate of the original while an ion beam (of a beam diameter 200 nm) may be projected, whereby metal may be deposited to form a non-reflective portion.

The stage may be moved back to the inspecting system for checking purpose, without unloading the original from the stage, and inspection may be made again. If any fault is found, the original may be conveyed again to the micro-processing system where repair of fault may be performed again.

In accordance with this embodiment of the present invention, as described, the original is not unloaded out of the stage during the sequential processes. Thus, there does not occur a positional deviation attributable to mounting/demounting of the original. Very high precision inspection and repair is thus assured.

There are cases wherein, in inspection/repair of a reflection type original, the pattern bearing surface of the original is not flat and it has some warp or curvature. This causes variation, with location, of the incidence angle of a light beam or a particle beam being projected on the surface of the original for inspection or repair of the original. If this occurs, it results in degradation of the precision of the inspection or repair.

Figure 3:
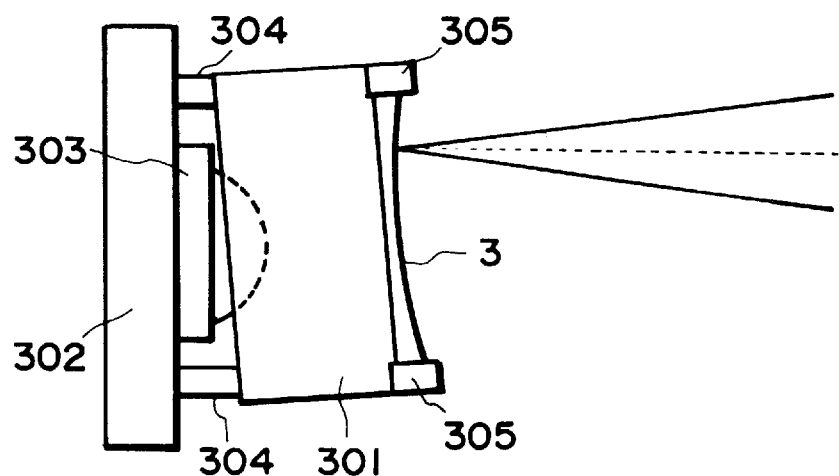
FIG. 3 is a schematic view for explaining the tilt operation of the tilt mechanism.

In consideration of it, the stage is equipped with a tilt mechanism, by which the tilt can be adjusted in accordance with the position of incidence of the beam. This assures that the light projected to the pattern bearing surface impinges perpendicularly thereto, irrespective to the position on the surface. FIG. 2 illustrates details of the structure of the original stage 31 having a tilt mechanism. The tilt mechanism comprises a member 303 having a function functioning as a spherical seat or an equivalent thereto, an expansion/contraction mechanism 304 (such as a displacement producing device comprising a piezoelectric device, for example) for applying tilt to the chuck 301, and a fixing member 305 which serves to prevent positional displacement due to acceleration applied to a member being held. These components are fixedly mounted on a member 301. There are at least three expanding/contracting elements so as to apply tilt in any direction. The reflection type original 3 is held fixed by the fixing member 305. Here, if as shown in FIG. 3 the pattern bearing surface of the reflection type original 3 is not flat but it comprises a concave or convex spherical surface, then the measurement and repairing operations are performed while executing the tilting and translating motion to adjust and maintain the perpendicularity of the surface to the axis of projected light.

If, for example, a reflection type original is made by coating and patterning a multilayered film mirror substrate of a curvature radius 200 mm with germanium of 300 nm and if it is designed to be used with a wavelength 13 nm, without application of any tilt to a central portion or to a peripheral potion, the measurement of reflectivity of the high reflectivity portion will result in a decreased reflectivity of 40% at a peripheral portion, spaced by 50 mm from the central portion having a reflectivity 55%, regardless of whether there is no difference in film structure between these portions. As compared therewith, if a tilt of 15 deg. is applied after translating motion of the original by 50 mm, substantially the same reflectivity (54%) as that at the central portion will be measured. Further, if the reflectivity of the non-reflective portion is measured while translationally moving the stage, point blank faults of about 1 micron, for example, can be found at a density of about $0.2/cm^2$. Also during the fault repairing operation, the tilt mechanism is used to maintain the perpendicularity between the pattern bearing surface and the axis of projected ion beam, constantly. This assures very accurate fault repair.

A fault of a reflection type original may reside not only in the pattern portion as described above but also in a multi-layered reflection film itself (the base of reflection type original). For example, a fault may frequently be observed in a multilayered film, which fault may be attributable to a particle remaining on the substrate after cleaning, or to a strain created by evaporation of a water drop. Such a fault may cause a variation in reflectivity of the reflection mirror and, as a result of it, there may occur non-uniformness in the reflection intensity of the original. While such a fault may desirably be removed completely prior to the formation of the multilayered film, practically it is difficult to accomplish. Thus, the inspection and repair may desirably be performed not only to a pattern portion but also to a multilayered film reflection mirror portion, which is the base of the reflection type original.

To this end, a multilayered reflection film before patterning is inspected by the inspection system, and evaluation of uniformness of reflectivity of the multilayered film is performed. Subsequently, a multilayered film portion with a fault, where variation of in reflectivity has measured, is removed by the micro-processing system and, thereafter, a multilayered film is formed again in that portion by deposition. By this, the fault of multilayered film is repaired.

If, for example, the multilayered film reflection mirror comprises constituent layers of Mo and Si, first the presence/absence of a pinhole-like or islet-like fault may be inspected by the inspecting system. Any fault detected may be removed in the micro-processing system by removing, by etching with an ion beam, a multilayered film material in a region around the fault until the base surface of the substrate may be exposed. Subsequently, while blowing a gas of $SiH_4$ and a gas of $Mo(CO)_6$ alternately and through a CVD process, a multilayered film of the same periodicity structure as of the original multilayered film may be formed thereon. In this manner, the fault can be repaired, and a multilayered film reflection mirror without, non-uniformness in reflectivity, can be prepared.

While the invention has been described with reference to the structures disclosed herein, it is not confined to the details set forth and this application is intended to cover such modifications or changes as may come within the purposes of the improvements or the scope of the following claims.

What is claimed is:

1. An X-ray mask inspecting and repairing system, comprising:
   inspecting means comprising an X-ray microscope for inspecting an X-ray mask having a multilayered reflection film for use in X-ray lithography, wherein said X-ray microscope uses a beam having a wavelength that is substantially the same as that to be used during X-ray lithography, and wherein the multilayered reflection film of the X-ray mask is designed to be used with a beam of that wavelength; and
   processing means for processing the X-ray mask on the basis of the inspection.

2. A system according to claim 1, wherein said inspecting means includes an illumination system having at least one of a plasma excitation X-ray source and a synchrotron radiation source.

3. A system according to claim 1, wherein said inspecting means includes an illumination system having spectroscopic means, and wherein said illumination system is adapted to perform at least one of Koehler illumination, critical illumination and coherent illumination.

4. A system according to claim 3, wherein said spectroscopic means includes a multilayered film reflection mirror.

5. A system according to claim 1, wherein said inspecting means includes a detection system having a detector which comprise one of a two-dimensional image sensor, a photodiode, an image multiplier tube and a micro-channel plate.

6. A system according to claim 1, wherein said processing means includes at least one of a convergent ion beam source, a laser beam source and an electron beam source.

7. A system according to claim 1, further comprising keeping means for keeping constituent elements, at least except for a light source, in a reduced pressure ambience.

8. A system according to claim 1, further comprising a stage for holding the X-ray mask and being movable between said inspecting means and said processing means.

9. A system according to claim 8, wherein said stage includes a tilt mechanism.

10. A system according to claim 1, wherein said inspecting means is operable to inspect any fault of a pattern of the X-ray mask, and wherein said processing means is operable to repair the pattern.

11. A system according to claim 1, wherein said inspecting means is operable to inspect any fault of a multilayered reflection film of the X-ray mask, and wherein said processing means is operable to repair the multilayered reflection film.

12. A system according to claim 1, wherein the wavelength is about 13 nm.

13. An X-ray inspecting method, comprising the steps of: p1 providing an X-ray microscope; and p1 inspecting, by use of the X-ray microscope, a reflection type mask having a multilayered film for use in X-ray lithography, wherein the X-ray microscope uses a beam having a wavelength substantially the same as that to be used during the X-ray lithography, and wherein the multilayered reflection film of the mask is designed to be used with a beam of that wavelength.

14. A method according to claim 13, wherein said inspection is made to inspect any fault of the reflection type mask.

15. A method according to claim 13, wherein said inspection is made to inspect any fault of a multilayered reflection film of the reflection type mask.

16. A method according to claim 13, further comprising repairing the mask on the basis of said inspection.

17. A method according to claim 16, further comprising inspecting again the mask by using the microscope.

18. A method according to claim 13, wherein said inspection and repair are performed in a reduced pressure ambience.

19. A method according to claim 13, wherein the wavelength is about 13 nm.

20. A reflection type mask for use in X-ray lithography and having been inspected and repaired in accordance with an X-ray inspecting method which comprises the steps of:
   providing an X-ray microscope; and
   inspecting, by use of the X-ray microscope, a reflection type mask having a multilayered reflection film for use in X-ray lithography, wherein the X-ray microscope uses a beam having a wavelength substantially the same as that to be used during the X-ray lithography, and wherein the multilayered reflection film of the mask is designed to be used with a beam of that wavelength.

21. A mask according to claim 20, wherein the wavelength is about 13 nm.

22. A device manufacturing method for use with a reflection type mask for X-ray lithography, said method comprising the steps of:

providing a reflection type mask having a multilayered reflection film for use in X-ray lithography;

providing an X-ray microscope; and inspecting, by use of the X-ray microscope, the reflection type mask, wherein the X-ray microscope uses a beam having a wavelength that is substantially the same as that to be used during the X-ray lithography, and wherein the multilayered reflection film of the X-ray mask is designed to be used with a beam of that wavelength.

23. A method according to claim 22, wherein the wavelength is about 13 nm.

* * * * *

UNITED STATES PATENT AND TRADEMARK OFFICE
CERTIFICATE OF CORRECTION

PATENT NO. : 5,808,312
DATED : September 14, 1998
INVENTOR(S) : YASUAKI FUKUDA

It is certified that error appears in the above-identified patent and that said Letters Patent is hereby corrected as shown below:

COLUMN 2,
Line 46, "advanced" should read --advanced,--; and
Line 47, "Theses" should read --These--.

COLUMN 4,
Line 43, "mirror" should read --mirrors--.

COLUMN 6,
Line 1, "radius" should read --radius of--;
Line 5, "may" should read --may be--;
Line 39, "having a function" should be deleted;
Line 61, "potion," should read --portion,--; and
Line 64, "55%," should read --of 50%,--.

COLUMN 7,
Line 44, "mirror without," should read --mirror, without--; and
Line 29, "variation of in reflectivity has measure," should read --a variation in reflectivity has been measured,--.

UNITED STATES PATENT AND TRADEMARK OFFICE
CERTIFICATE OF CORRECTION

PATENT NO. : 5,808,312

DATED : September 14, 1998

INVENTOR(S) : YASUAKI FUKUDA

It is certified that error appears in the above-identified patent and that said Letters Patent is hereby corrected as shown below:

COLUMN 8,
Line 9, "comprise" should read --comprises--; and
Line 34, "p1 providing" should read --¶ providing--, and
"p1 inspecting," should read --¶ inspecting,--.

Signed and Sealed this

Seventh Day of September, 1999

Q. TODD DICKINSON

Attest:

Attesting Officer

Acting Commissioner of Patents and Trademarks